United States Patent [19]

Foguet et al.

[11] Patent Number: 5,643,927

[45] Date of Patent: Jul. 1, 1997

[54] 4-P-FLUOROBENZOYL-1-PIPERIDINYL-PROPOXY-CHROMEN-4-ONE DERIVATIVES, THEIR PREPARATION AND THEIR USE IN THE TREATMENT OF PSYCHOSIS AND SCHIZOPHRENIA

[75] Inventors: Rafael Foguet; Jordi Bolós; Aurelio Sacristán; José A. Ortiz, all of Barcelona, Spain

[73] Assignee: Ferrer Internacional, S.A., Barcelona, Spain

[21] Appl. No.: 532,791

[22] PCT Filed: Mar. 17, 1995

[86] PCT No.: PCT/EP95/01008

§ 371 Date: Dec. 12, 1995

§ 102(e) Date: Dec. 12, 1995

[87] PCT Pub. No.: WO95/25733

PCT Pub. Date: Sep. 28, 1995

[30] Foreign Application Priority Data

| | | | |
|---|---|---|---|
| Mar. 18, 1994 | [ES] | Spain | 9400581 |
| Jul. 1, 1994 | [ES] | Spain | 9401437 |
| Jan. 30, 1995 | [ES] | Spain | 9500163 |

[51] Int. Cl.⁶ .................... A61K 31/445; C07D 405/12
[52] U.S. Cl. ............................. 514/320; 546/196
[58] Field of Search ........................... 546/196; 514/320

[56] References Cited

U.S. PATENT DOCUMENTS

| | | | |
|---|---|---|---|
| 3,576,810 | 4/1971 | Duncan | 546/225 |
| 5,424,318 | 6/1995 | Sugimoto | 514/325 |

OTHER PUBLICATIONS

Tomino et al. "Preparation of benzofuranyloxyalkylamine derivatives as antiarrhythmics and psychotropics" CA 114:81563. 1991.

Dorland "Medical Dictionary" Saunders Co., p. 499. 1982.

Katritzky et al "Heterocyclic chemistry" Cambridge, pp. 78, 91, 190. 1964.

Primary Examiner—Ceila Chang

[57] ABSTRACT

The present invention relates to new chromene compounds of the general formula (I):

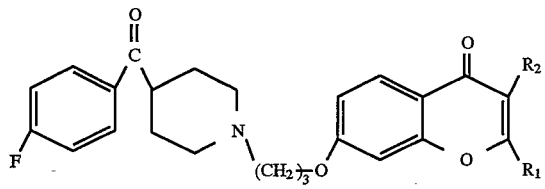

wherein $R_1$ and $R_2$ are hydrogen, alkyl having from 1 to 4 carbon atoms, halogen, trifluoromethyl, optionally substituted phenyl, or hydroxymethyl, as well as their pharmaceutically acceptable addition salts.

These compounds are useful in the treatment of psychosis and schizophrenia.

7 Claims, No Drawings

4-P-FLUOROBENZOYL-1-PIPERIDINYL-PROPOXY-CHROMEN-4-ONE DERIVATIVES, THEIR PREPARATION AND THEIR USE IN THE TREATMENT OF PSYCHOSIS AND SCHIZOPHRENIA

This application is a 371 of PCT/EP95/01008 filed Mar. 17, 1995.

The present invention relates to new chromene compounds having the general formula (I):

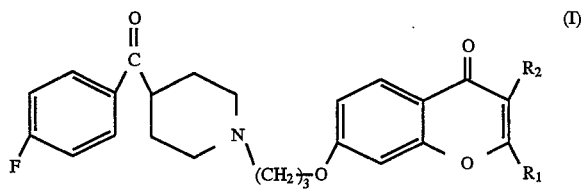

wherein $R_1$ and $R_2$ are hydrogen, alkyl having from 1 to 4 carbon atoms, halogen, trifluoromethyl, optionally substituted phenyl, or hydroxymethyl, as well as their pharmaceutically acceptable addtion salts.

Among the pharmaceutically acceptable salts, hydrochloride is preferred.

Said phenyl group may be substituted with 1 to 3 substituents independently selected from $C_1$-$C_4$ alkyl, hydroxy, $C_1$-$C_4$ alkoxy, halogen, amino, mono or di-$C_1$-$C_4$ alkylamino and nitro.

The compounds of the general formula (I) are obtained according to Scheme I. In effect, the alkylation of 4-(p-fluorobenzoyl)-piperidine (II) with a 7-(3-halopropoxy) chromen-4-one of general formula (III), wherein X is chlorine, bromine or iodine and $R_1$ and $R_2$ are as defined for (I), provides the compounds of the invention. The reaction occurs conveniently in a nonpolar solvent and in the presence of a base.

Acetonitrile is appropriate as a nonpolar solvent, and as a base it is useful to employ an alkali metal carbonate or hydrogen carbonate. Potassium iodide can be used as a catalyst. The reaction occurs under heating, preferably at the boiling temperature of the mixture. Intermediate (II) can be purchased from commercial source. This reaction can be illustrated according to Scheme 1.

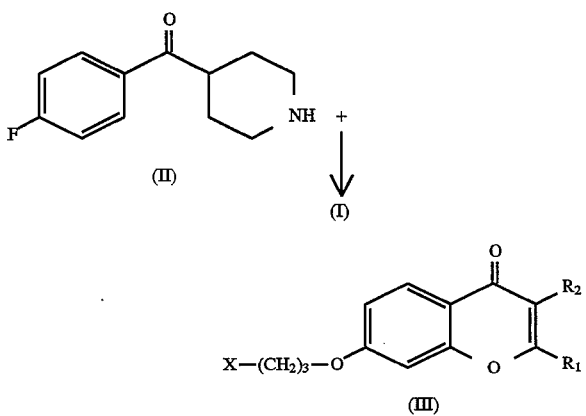

The intermediates of the general formula (III) wherein X is chlorine, bromine or iodine and $R_1$ and $R_2$ are hydrogen, alkyl having from 1 to 4 carbon atoms, halogen, trifluoromethyl, optionally substituted phenyl, may be prepared, although not in a limitative manner, a) by alkylation of the corresponding 7-hydroxy-chromen-4-ones of general formula (IV) wherein $R_1$ and $R_2$ are as defined in (I) with 1-bromo-3-halopropane of general formula (V) wherein X is as defined in (III), or b) by cyclization from the corresponding 4-(3-halopropoxy)-2-hydroxyacetophenones of general formula (VI) wherein X is as defined in the preceding structure, all of this according to Scheme 2. In this scheme, [Y] is a halogenating agent which is able to introduce a chlorine, bromine or iodine atom, such as tert-butyl hypochlorite, chlorine, bromine or iodine. The spontaneous intramolecular cyclization of the intermediates of general formula (VIII) in the reaction medium leads to the intermediates of general formula (III) when $R_1$ is hydrogen and $R_2$ is as defined for Y.

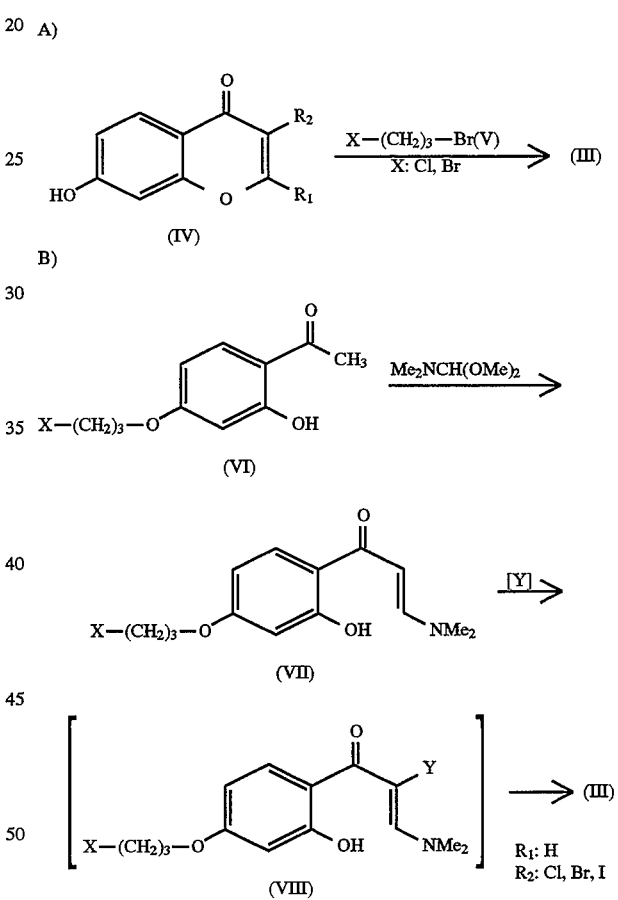

The intermediates of the general formula (III) wherein X is chlorine, bromine or iodine, $R_1$ is hydrogen and $R_2$ is hydroxymethyl may be prepared through two steps from the 4'-(halopropoxy)-2'-hydroxy-acetophenones of general formula (VI) by alkylation in dimethylformamide with phosphoryl chloride followed by addition on ice and subsequent reduction of the so-formed 7-(3-halopropoxy)-3-formyl-chromen-4-ones of general formula (IX) wherein X is as defined in the preceding structures with sodium borohydride according to conventional procedures of organic chemistry as shown in Scheme 2'.

Scheme 2'

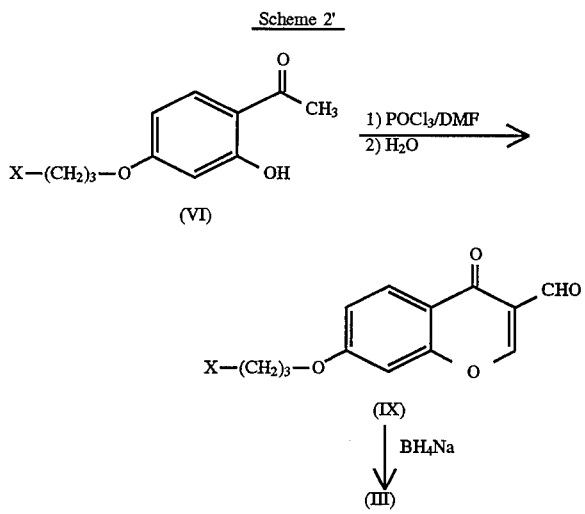

In turn, the raw material required for performing the reactions shown in these schemes may be obtained either from commercial sources or according to conventional procedures of organic chemistry.

Chromene compounds containing amine groups are known in the patent literature, and their use for treating various diseases is recommended. EP Patent No. 546389 discloses substituted piperidyl-methyl chromanes as dopamine and serotonin receptor inhibitors which are potentially useful for treating CNS diseases, such as anxiety, depression, psychosis, Alzheimer's disease, etc. EP Patent No. 441506 discloses 3-piperidino-4-hydroxy-chromanes that can be used in the treatment of CNS diseases, such as stroke, Alzheimer's disease, Parkinson's disease and Huntington's disease. PCT Patent application No. 9012795 discloses substituted chromanes that are potentially useful for treating CNS diseases, such as aggressive behaviour, delirium and confusion, and impotence. PCT Patent application No. 8702359 discloses aminoalcohols from the family of dihydrobenzothiophene and thiochromane having antihypertensive, antithrombotic, hypolipidemic, spasmolytic, calcium antagonist and neuroleptic actions. U.S. Pat. No. 4,678,787 discloses 4H-1-benzopyran-4-ones and their analogs containing sulfur, which are potentially useful to treat psychosis and schizophrenia. U.S. Pat. No. 4617314 discloses dihydrobenzofuranyl- and benzopyranyl-carboxamides having antidopamine, antiemetic and methamphetamine potentiating actions. EP Patent No. 89781 discloses 7-substituted 5-hydroxy-3,4-dihydrobenzopyran compounds as antidiarrheals, antiemetics, antinauseants, tranquilizers, diuretics, antitussives and antiglaucoma agents. DE Patent No. 2037852 discloses N-arylpropyl(2)-N'-aryl-piperazines as sedatives, neuroleptics, tranquilizers, bronchospasmolytics and hypotensors. U.S. Pat. No. 4,428,955 discloses benzopyranyl ether derivatives as histamine antagonists. U.S. Pat. No. 4,320,128 discloses 7-(2-hydroxy-3-piperazino-propoxy)-3,3-dimethyl chromanone having antihypertensive action.

Thus, the compounds of formula (I) are different from the compounds disclosed in the aforesaid patents and prove not to be obvious in view of the prior art described in these patents. The compounds exhibit an interesting profile as neuroleptics, as evidenced by both biochemical and pharmacological data. In effect, the biochemical tests revealed an intense action of these compounds on various receptors that are generally considered to be involved in the neuroleptic action ($\sigma$, $D_2$ $5HT_2$ receptors, B. L. Largent et al: "Eur. J. Pharmacol.", 155, 345–7, 1988; $5HT_{1a}$ receptors, B. A. McMillen et al: "Drug Devo Res.", 12, 53–62, 1988; $D_3$ receptors, P. Sckoloff et al: "Nature", 347, 146–151, 1990). Specific binding to $\sigma$, $D_2$, $D_3$, $5H_2$ and $5HT_{1a}$ receptors has been tested as follows:

$\sigma$ receptors: A 2-nM solution of radioactive 3-PPP ((+) [$^3$H]3-[3-hydroxyphenyl]-N-(1-propyl)-piperidine), which acts as a specific ligand, was incubated with the membrane corresponding to 40 mg of guinea-pig total brain for 90 min at 25° C. buffered at pH 8.5 with Tris.HCl. Thus, total binding of ligand to membranes was attained. Non-specific binding was then determined by adding a micromolar concentration of unlabelled 3-PPP. $IC_{50}$ values (inhibitory concentration 50%) were calculated from the inhibition rate of the specific binding obtained by adding eleven different concentrations of the compounds to be tested. After the incubation was completed, the samples were filtered through a glass fiber filter and then washed three times with Tris.HCl buffer. The amount of receptor-bound radioactivity was retained on the membrane and determined by liquid scintillation counting.

$D_2$ receptors: A 2-nM solution of radioactive spiperone ([$^3$H]spiperone), which acts as a specific ligand, was incubated with the membrane corresponding to 20 mg of rat striatum for 20 min at 35° C. buffered at pH 7.4 with Tris.HCl. The non-specific binding was then determined by addition of a micromolar concentration of unlabelled spiperone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$D_3$ receptors: A 0.1 nM solution of radioactive YM-0951 ([$^3$H]YM-0951), which acts as a specific ligand, was incubated with the membrane provided by RBI obtained from mouse fibroblasts (CCL 1,3) for 15 min at 37° C., buffered at pH 7.4 with Tris.HCl. The non-specific binding was then determined by addition of a micromolar concentration of unlabelled 7-OH-DPAT. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$5HT_{1a}$ receptors: A 1 nM solution of radioactive 5-OH-DPAT ([$^3$H]5-OH-DPAT), which acts as a specific ligand, was incubated with the membrane corresponding to 1 mg of rat cortex for 20 min at 35° C. buffered at pH 7.4 with Tris.HCl. Non-specific binding was then determined by addition of a 20 micromolar concentration of unlabelled buspirone. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

$5HT_2$ receptors: A 0.5 nM solution of radioactive ketanserin ([$^3$H]ketanserin), which acts as a specific ligand, was incubated with the membrane corresponding to 1 mg of rat cortex for 30 min at 35° C. buffered at pH 7.4 with Tris.HCl.

Non-specific binding was then determined by addition of 5 micromolar concentration of unlabelled mianserin. $IC_{50}$ (inhibitory concentration 50%) was calculated from the inhibition rate of the specific binding obtained by addition of eleven different concentrations of the compounds to be tested. After the incubation was completed, the sample was filtered through a glass fiber filter and then washed three times with Tris.HCl buffer. The amount of receptor-bound radioactivity was retained on the membrane and determined by liquid scintillation counting.

The comparative biochemical results of the compounds of Examples 1, 2, 3 and 4 versus several reference compounds are presented in Table 1. Values are expressed as $IC_{50}$ in molar concentrations.

animals. After 60 minutes, p-chloro-amphetamine was subcutaneously injected at a dose of 5 mg/kg, and the animals were immediately placed in respective cages. The device was started and the motor activity of animals was monitored for 90 minutes. The results obtained in this test are presented in Table 2 (A).

B) Inhibition of apomorphine-induced hyperactivity:

Male Swiss mice weighing 22–26 g were used. One week prior to experiment, animals were kept in our facilities at a temperature of 20°–22° C. and 12/12 h light-dark cycle, and had free access to food and water.

Motor activity was measured using a DAS 16 computer-assisted Actimeter (Actisystem, Panlab) which records data from four sensory units. These units detect the activity via

TABLE 1

| | $IC_{50}$ (M) | | | | | | |
|---|---|---|---|---|---|---|---|
| | σ | $D_2$ | $D_3$ | $5HT_{1A}$ | $5HT_2$ | $D_2/σ$ | $D_2/5HT_2$ |
| Example 1 | $1.46 \times 10^{-8}$ | $4.36 \times 10^{-7}$ | $6.88 \times 10^{-8}$ | $1.56 \times 10^{-6}$ | $1.71 \times 10^{-8}$ | 29.9 | 25.5 |
| Example 2 | $7.99 \times 10^{-7}$ | $3.74 \times 10^{-7}$ | $8.55 \times 10^{-7}$ | $1.57 \times 10^{-6}$ | $5.66 \times 10^{-8}$ | 0.47 | 6.61 |
| Example 3 | $2.43 \times 10^{-7}$ | $1.29 \times 10^{-7}$ | $1.94 \times 10^{-7}$ | $7.64 \times 10^{-7}$ | $8.20 \times 10^{-8}$ | 0.53 | 1.57 |
| Example 4 | — | $1.90 \times 10^{-7}$ | — | — | $4.74 \times 10^{-8}$ | — | 4.01 |
| Haloperidol | $2.14 \times 10^{-9}$ | $1.23 \times 10^{-8}$ | — | $1.12 \times 10^{-5}$ | $1.04 \times 10^{-7}$ | 5.75 | 0.12 |
| BMY-14802 | $4.90 \times 10^{-8}$ | $1.59 \times 10^{-5}$ | — | $4.04 \times 10^{-7}$ | $1.15 \times 10^{-6}$ | 324 | 13.8 |
| 7-OHDPAT | — | — | 6.018 | — | — | — | — |
| Risperidone | — | $7.61 \times 10^{-9}$ | — | $4.31 \times 10^{-7}$ | $4.06 \times 10^{-10}$ | — | 18.7 |

From the results in the above table, it can be concluded that the compounds of this invention are characterized by a genuine neuroleptic profile, since advantageously their specificity over $5HT_2$ receptors versus $D_2$ receptors according to $D_2/5HT_2$ ratios is higher than that of haloperidol. In addition, the specificity of the compound of Ex. 1 over σ receptors versus $D_2$ receptors is also higher than that of haloperidol and surpasses BMY-14802 and risperidone in $D_2/5HT_2$ ratio. In addition, the compound is active on $D_3$ receptors in the same order as 7-OH-DPAT. All this confers potentially valuable properties on the compounds of this invention as neuroleptics, which are useful in psychosis and schizophrenia, and no extrapyramidal effects are attributed to their interaction with $D_2$ receptors.

The neuroleptic activity of the compounds of this invention was confirmed in Animal Pharmacology by oral testing of the inhibition of p-chloro-amphetamine-induced hyperactivity (T. G. Heffner et al: "J.Pharmacol.Exp.Ther.", 251, 105, 1989), inhibition of apomorphine-induced hyperactivity (A. Puech et al: "Eur. J.Pharmacol.", 50, 291–300, 1978) and inhibition of apomorphine-induced climbing behaviour (P. Protais et al: "Psychopharmacology", 50, 1–6, 1976).

The three pharmacological tests were performed as follows:

A) Inhibition of p-chloro-amphetamine-induced hyperactivity;

Male Swiss mice weighing 22–26 g were used. One week prior to experiment, animals were kept in our facilities at a temperature of 20°–22° C. and 12/12 h light-dark cycle, and had free access to food and water.

Motor activity was measured using a DAS 16 computer-assisted Actimeter (Actisystem, Panlab) which records data from four sensory units. These units detect the activity via resonance frequency oscillation in LC network. The device consists of a top transparent cage for placing of animals and a lower command panel for starting and calibration of it, as well as a system for animal activity detection.

Animals were administered orally with test drug at time 0 and then placed into each Actimeter cage in groups of three resonance frequency oscillation in LC network. The device consists of a top transparent cage for placing of animals and a lower command panel for starting and calibration of it, as well as a system for animal activity detection.

Animals were administered orally with test drug at time 0 and then placed into each Actimeter cage in groups of three animals. After 30 minutes, apomorphine was subcutaneously injected at a dose of 1 mg/kg, and the animals were immediately placed in respective cages. The device was started and the motor activity of animals was monitored for 60 minutes. The results obtained in this test are presented in Table 2 (B).

C) Inhibition of apomorphine-induced climbing behaviour:

Male Swiss mice weighing 22–26 g were used. One week prior to experiment, animals were kept in our facilities at a temperature of 20°–22° C. and 12/12 h light-dark cycle, and had free access to food and water. Two hours prior to experiment, the animals were placed in individual cages without access to food.

Animals were administered orally with either test drug or 0.25% agar at time 0. After 60 minutes, apomorphine was subcutaneously injected at a dose of 1 mg/kg, and after further 60 minutes the animal's behaviour was assessed. Two additional assessments were performed at 10-min intervals.

For assessment, each animal was placed on the bottom of a small upright box (7.5×4.5 cm). The walls of the box were made of translucent methacrylate except one of the lateral surfaces (7.5 cm wide) which was a 3-mm wire mesh. The position of the animal was scored for 2 minutes according to the following criteria: 0=four paws on the floor; 1=three paws on the floor; 2=two paws on the floor; 3=one paw on the floor; and 4=four paws holding the wire mesh. If an animal keeps several positions within the 2-min observation, the seconds elapsed in each position will be recorded. Finally, mean scoring was calculated. The results obtained in this test are presented in Table 2 (C).

TABLE 2

| | ED$_{50}$ (mg/kg) | | |
|---|---|---|---|
| | Test (A) | Test (B) | Test (C) |
| Example 1 | 3.2 | 2.5 | 6.4 |
| Example 2 | 2.1 | 6.1 | 25 |
| Example 3 | 1.8 | 1.6 | 4.9 |
| Example 4 | — | — | 3.2 |
| Example 5 | 5.9 | 11.1 | >25 |
| Example 6 | 3.3 | >25 | >25 |
| Example 7 | 2.6 | 6.2 | 9.1 |

The compounds of this invention are found to be potentially useful as neuroleptics for treating psychosis and schizophrenia. Among the compounds described in this invention, the compound of Example 1, 7-[3-(4-p-fluorobenzoyl-1-piperidinyl)propoxy]-chromen-4-one hydrochloride, the compound of Example 3, 7-[3-(4-p-fluorobenzoyl-1-piperidinyl)propoxy]-3-methyl-chromen-4-one hydrochloride, and the compound of Example 4, 3-Hydroxymethyl-7-[3-(4-p-fluorobenzoyl-1-piperidinyl)propoxy]chromen-4 -one hydrochloride, are preferred. In fact, the compound of Example 1 was biochemically the most specific over 5HT$_2$ receptors versus D$_2$ receptors. The compound of Example 3 was very active in animal pharmacological tests and, moreover, its extrapyramidal effects were not very important; the oral administration of this compound to rats at a dose of 50 mg/kg (over 10 times ED$_{50}$—Test C) caused catalepsy in only 60% of treated animals 3 hours after administration and inhibited stereotypy in only 23% of animals. The compound of Example 4 was also very active in animal pharmacological tests and did not show very important extrapyramidal effects either; in effect, in rat oral testing, it was necessary to administer a dose of 15 mg/kg of product so that catalepsy could occur in 50% of treated animals.

EXAMPLE 1

7-[3-(4-p-fluorobenzoyl-1-piperidinyl)propoxy]chromen-4-one hydrochloride

To a solution of 3.9 g (18.8 mmole) of 4-p-fluorobenzoyl-piperidine and 4.5 g (18.8 mmole) of 7-(3-chloropropoxy) chromen-4-one in 250 ml of acetonitrile, 2.7 g (18.8 mmole) of anhydrous potassium carbonate and 0.2 g of potassium iodide were added. The resulting suspension was refluxed for 24 hours, then cooled, filtered, and the filtrate was evaporated to dryness. The oil obtained was dissolved in dichloromethane, washed with NaCl saturated solution, dried over sodium sulfate and evaporated. The residue was dissolved in isopropanol and precipitated by addition of HCL solution in isopropanol to provide 2.2 g (26%) of product.

Elemental analysis for C$_{24}$H$_{24}$FNO$_4$.HCl: (calculated) C 64.64, H 5.65, N 3.14, Cl 7.95; (found) C 64.34, H 5.77, N 2.93, Cl 8.13. Melting point: 235°–238° C. (i-PrOH).

IR (KBr): 3200–3600, 2930, 2300–2800, 2680. 1650, 1630, 1595, 1445, 1270, 1230 cm$^{-1}$.

$^1$H-NMR (d$_6$-DMSO): 2.01 (m, 4H, piper-3H and -5H), 2.30 (m, 2H, O—CH$_2$—CH$_2$), 3.13 (m, 2H, piper-2H$_{ax}$ and -6H$_{ax}$), 3.24 (t a, J=6Hz, 2H, N—CH$_2$—CH$_2$—CH$_2$—O), 3.61 (d a, J=10.2Hz, 2H, piper-2H$_{eq}$ and -6H$_{eq}$), 3.75 (m, 1H, 4-H), 4.25 (t a, J=6Hz, 2H, O—CH$_2$), 6.29 (d, J=6.3Hz, 1H, 3-H), 7.08 (dd, J=9 and 2 Hz, 1H, 6-H), 7.16 (d, J=2Hz, 1H, 8-H), 7.40 (t, J=9Hz, 2H, Ph-3H and -5H), 7.96 (d, J=9Hz, 1H, 5-H), 8.11 (dd, J=9 and 6Hz, 2H, Ph-2H and -6H), 8.25 (d, J=6Hz, 1H, 2-H).

$^{13}$C-NMR (d$_6$-DMSO): 22.93 (O—CH$_2$—CH$_2$), 25.46 (piper-3C and 5C), 40.03 (piper-4C), 50.85 (piper-2C and -6C), 53.18 (O—CH$_2$—CH$_2$—CH$_2$—N), 65.77 (O—CH$_2$), 101.77 (8-C), 111.91 (3-C), 114.62 (6-C), 115.65 (d, J=21.7Hz, Ph-3C and -5C), 117.90 (4a-C), 126.13 (5-C), 131.04 (d, J=9.2Hz, Ph-2C and -6C), 131.52 (d, J=3.5Hz, Ph-1C), 156.16 (2-C), 157.34 (8a-C), 162.31 (7-C), 164.78 (d, J=250.4Hz, Ph-4C), 175.25 (4-C), 199.09 (Ph-C=O).

EXAMPLE 2

7-[3-(4-p-fluorobenzoyl-1-piperidinyl)propoxy]-2-methyl-chromen-4-one hydrochloride a) General procedure of alkylation of 4-(p-fluorobenzoyl) piperidine A mixture of 4.5 9 (19 mmole) of 4-(p-fluorobenzoyl) piperidine, 19 mmole of the corresponding 7-(3-halopropoxy) chromen-4-one, 2.7 9 (19 mmole) of anhydrous potassium carbonate and 0.2 9 of potassium iodide in 250 ml of acetonitrile was heated at reflux for 24 hours. The mixture was allowed to cool and filtered, and the filtrate was evaporated to dryness. The residue was dissolved in dichloromethane, washed with sodium clorhide saturated solution, dried over anhydrous sodium sulfate and evaporated. The product was redissolved in isopropanol and precipitated by addition of hydrogen chloride solution. The precipitate was collected by filtration, washed with isopropanol and recrystallized from methanol-ethyl ether.

b) 7-[3-(4-p-fluorobenzoyl-1-piperidinyl)propoxy]-2-methyl-chromen-4-one hydrochloride According to the general procedure described in a), from 7-(3-chloropropoxy)-2-methyl-chromen-4-one, the compound was obtained as a solid (yield=77%), melting point 250°–253° C.

Elemental analysis calculated for C$_{25}$H$_{26}$FNO$_4$.HCl: C 65.29; H 5.92; N 3.05; Cl 7.70. Found: C 64.93; H 5.83; N 3.01; Cl 7.63.

IR (KBr): 3200–3600, 2300–2500, 1685, 1650, 1610, 1445, 1390 cm$^{-1}$.

$^1$H-NMR (CDCl$_3$): 1.87 (m, 4H, piper-3H and -5H), 2.03 (quint, J=6.7 Hz 2H, OCH$_2$—CH$_2$), 2.13 (m, 2H, piper-2H$_{ax}$ and -6H$_{ax}$), 2.36 (s, 3H, CH$_3$), 2.55 (t, J=6.7 Hz, 2H, OCH$_2$—CH$_2$—CH$_2$), 3.02 (d a, J=10.5 Hz, 2H, piper-2H$_{eq}$ and -6H$_{eq}$), 3.22 (m, 1H, piper-4H), 4.12 (t, J=6.7 Hz, 2H, OCH$_2$), 6.10 (s, 1H, 3-H), 6.84 (d, J=2.4 Hz, 1H, 8-H), 6.93 (dd, J=8.9 and 2.4 Hz,1H, 6-H), 7.14 (t, J=8.9 Hz, 2H, Ph-2H and -5H), 7.97 (dd, J=8.9 and 5.3 Hz, 2H, Ph-2H and -5H), 8.06 (d, J=8.9Hz, 1H, 5-H).

$^{13}$C-NMR (CDCl$_3$): 20.39 (CH$_3$), 23.67 (piper-3C and -5C), 25.89 (OCH$_2$CH$_2$), 35.62 (piper-4C), 49.43 (piper-2C and -6C), 52.13 (O—CH$_2$CH$_2$CH$_2$), 65.28 (OCH$_2$), 100.61 (8-C), 109.95 (3-C), 114.21 (6-C), 116.05 (d, J=22 Hz, Ph-3C and -5C), 117.26 (4a-C), 126.78 (5-C), 130.94 (d, J=7 Hz, Ph-6C and -2C), 131.10 (Ph-1C), 157.89 (8a-C), 162.30 (7-C), 165.85 (d, J=255 Hz, Ph-4C), 166.22 (2-C), 177.93 (4-C), 200.38 (Ph-C=O).

EXAMPLE 3

7-[3-(4-p-fluorobenzoyl-1-piperidinyl)propoxy]-3-methyl-chromen-4-one hydrochloride The compound was obtained as a solid (yield=50%), melting point 224°–227° C. (d).

Elemental analysis calculated for C$_{25}$H$_{26}$FNO$_4$.HCl: C 65.28; H 5.99; N 3.15; Cl 7.40. Found: C 64.97; H 5.98; N 3.08; Cl 7.23.

IR (KBr): 3200–3500, 2400–2900, 1680, 1640, 1595, 1450, 1250 cm$^{-1}$.

¹H-NMR (CD₃OD): 1.90 (s, 3H, CH₃), 2.02 (m, 4H, piper-3H and -5H), 2.31 (m, 2H, OCH₂CH₂), 3.12 (m, 2H, piper-2H$_{ax}$ and -6H$_{ax}$), 3.24 (t a, J=6 Hz, 2H, piper-2H$_{eq}$ and -6H$_{eq}$), 3.76 (m, 1H, 4-H), 4.23 (t, J=6 Hz, 2H, OCH₂), 7.05 (d, J=9 Hz, 1H, 6-H), 7.11 (s, 1H, 8-H), 7.40 (t, J=9 Hz, 2H, Ph-3H and -5H), 7.96 (d, J=9 Hz, 1H, 5-H), 8.12 (dd, J=9 and 5.5 Hz, 2H, Ph-2H and -6H), 8.22 (s, 1H, 2-H).

¹³C-NMR (CD₃OD): 10.90 (CH₃), 23.28 (OCH₂CH₂), 25.78 (piper-3C and -5C), 40.41 (piper-4C), 51.19 (piper-2C and -6C), 53.56 (O—CH₂CH₂CH₂), 66.12 (OCH₂), 101.16 (8-C), 114.79 (6-C), 115.98 (d, J=22 Hz, Ph-3C and -5C), 116.99 (4a-C), 119.59 (3-C), 126.43 (5-C), 131.39 (d, J=9 Hz, Ph-2C and -6C), 131.85 (d, J=3 Hz, Ph-1C), 152.47 (2-C), 157.80 (8a-C), 162.38 (7-C), 165.11 (d, J=250 Hz, Ph-4C), 176.25 (4-C), 199.61 (Ph-C=O).

EXAMPLE 4

3-Hydroxymethyl-7-[3-(4-p-fluorobenzoyl-1-piperidinyl)propoxy]-chromen-4-one hydrochloride A mixture of 1.6 g (6 mmole) of 7-(3-chloropropoxy-3-(hydroxymethyl)chromen-4-one, 1.2 g (6 mmole) de 4-(p-fluorobenzoyl)piperidine, 2 g (14 mmole) of anhydrous potassium carbonate and 0.5 g of potassium iodide in 30 ml of acetonitrile was heated for 24 hours at reflux, allowed to cool, filtered, and the filtrate was evaporated to dryness. The residue was dissolved in dichloromethane, washed with saturated sodium chloride solution, dried over anhydrous sodium sulfate, and evaporated. The product was dissolved in acetone and precipitated by addition of a hydrogen chloride solution. The precipitate was collected by filtration, washed with acetone, and recrystallized from methanol-ethyl ether to give 0.5 g (18%) of a solid, melting point 217°–218° C. (d).

Elemental analysis. Calculated for $C_{25}H_{26}FNO_5 \cdot HCl$: C, 63.09; H, 5.72; N, 2.94; Cl, 7.45. Found: C, 62.89; H, 5.91; N, 2.72; Cl, 7.30.

IR(KBr): 3100–3700, 2300–2800, 1680, 1645, 1600, 1245 cm⁻¹.

¹H-NMR (d₆-DMSO): 1.90–2.15 (m, 4H, piper-3H and -5H), 2.29 (m, 2H, —CH₂—CH₂), 3.20 (m, 2H, piper-2H$_{ax}$ and -6H$_{ax}$), 3.33 (m, 2H, N—CH₂—CH₂), 3.70 (da, J=10Hz, 2H, piper-2H$_{eq}$ and -6H$_{eq}$), 3.78 (m, 1H, piper-4H), 4.26 (t, J=6Hz, 2H, O—CH₂CH₂), 4.41 (s, 2H, CH₂—OH), 7.08 (dd, J=9 and 2Hz, 1H, 6-H), 7.12 (d, J=2Hz, 1H, 8-H), 7.35 (t, J=9Hz, 2H, Ph-3H and -5H), 8.02 (d, J=9Hz, 1H, 5-H), 8,11 (dd, J=9 y 6Hz, 2H, Ph-2H and -6H), 8,14 (s, 1H, 2-H), 10.80 (sa, 1H, OH).

¹³C-NMR (d₆-DMSO): 23.29 (O—CH₂—CH₂), 25.81 (piper-3C and -5C), 39.90 (piper-4C), 51.22 (piper-2C and -6C), 53.53 (N—CH₂ CH₂), 55.42 (CH₂—OH), 66.08 (O—CH₂CH₂), 101.30 (8-C), 114.93 (6-C), 115.99 (d, J=21, 6Hz, Ph-3C and -5C), 117.20 (4a-C), 123.89 (3-C), 126.38 (5-C), 131.38 (d, J=9Hz, Ph-2C and -6C), 131.85 (Ph-1C), 153.11 (2-C), 157.69 (8a-C), 162.52 (7-C), 165.11 (d, J=250, 4Hz, Ph-4C), 175.24 (4-C), 199.39 (Ph-C=O).

EXAMPLE 5

7-[3-(4-p-fluorobenzoyl-1-piperidinyl)propoxy]-2-trifluoromethyl-chromen-4-one hydrochloride The compound was obtained as a solid (yield=41%), melting point >250° C.

Elemental analysis calculated for $C_{25}H_{23}F_4NO_4 \cdot HCl$: C 58.43; H 4.71; N 2.73; Cl 6.90. Found: C 58.07; H 4.52; N 2.74; Cl 6.78.

IR (KBr): 3200–3600, 2300–2600, 1670, 1655, 1605, 1430, 1205 cm⁻¹.

¹H-NMR (d₆-DMSO): 2.01 (m, 4H, piper-3H and -5H), 2.29 (m, 2H, OCH₂CH₂), 3.15 (m, 2H, piper-2H$_{ax}$ and -6H$_{ax}$), 3.29 (m, 2H, OCH₂CH₂CH₂), 3.63 (d a, J=10 Hz, 2H, piper-2H$_{eq}$ and -6H$_{eq}$), 3.75 (m, 1H, 4-H), 4.27 (t a, J=6 Hz, 2H, OCH₂), 6.90 (s,1H, 3-H), 7.14 (dd, J=8.7 and 2 Hz, 1H, 6-H), 7.29 (d, J=2 Hz, 1H, 8-H), 7.34 (t, J=8.7 Hz, 2H, Ph-3H and -5H), 8.01 (d, J=8.7 Hz, 1H, 5-H), 8.10 (t a, J=8.7 Hz, 2H, Ph-2H and -6H).

¹³C-NMR (d₆-DMSO): 23.28 (OCH₂CH₂), 25.84 (piper-3C and -5C), 40.11 (piper-4C), 51.29 (piper-2C and 6C), 53.51 (OCH₂CH₂CH₂), 66.17 (OCH₂), 101.43 (8-C), 110.75 (3-C), 115.77 (d, J=22 Hz, Ph-3C and -5C), 116.17 (6-C), 118.52 (q, J=272Hz, CF₃),126.60 (5-C), 131.31 (d, J=10 Hz, Ph-2C and 6C), 131.63 (d, J=3 Hz, Ph-1C), 150.51 (q, J=39Hz, 2-C), 156.89 (8a-C), 163.55 (7-C), 165.07 (d, J=250 Hz, Ph-4C), 174.84 (4-C), 198.97 (Ph-C=O).

EXAMPLE 6

7-[3-(4-p-fluorobenzoyl-1-piperidinyl)propxy]-2-phenyl-chromen-4-one hydrochloride The compound was obtained as a solid (yield=53%), melting point 259°–262° C. (d).

Elemental analysis calculated for $C_{30}H_{28}FNO_4 \cdot HCl$: C 69.03; H 5.60; N 2.58; Cl 6.79. Found: C 68.86; H 5.52; N 2.56; Cl 6.50.

¹H-NMR (CDCL₃—CD₃OD): 2.20 (m, 4H, piper-3H and -5H), 2.45 (m, 2H, OCH₂CH₂), 3.30 (m, 2H, piper-2H$_{ax}$ and -6H$_{ax}$), 3.48 (m, 2H, OCH₂CH₂), 3.75 (d a, J=12 Hz, 2H, piper-2H$_{eq}$ and -6H$_{eq}$), 3.90 (m, 1H, 4-H), 4.29 (t a, J=5.4 Hz, 2H, OCH₂), 6.80 (s, 1H, 3-H), 7.04 (d, J=9 Hz, 1H, 6-H), 7.11 (d, J=2.4 Hz, 1H, 8-H), 7.21 (t, J=8.7 Hz, 2H, Ph-3H and -5H), 7.56 (m, 3H, 2-Ph-3H -4H and -5H), 7.96 (d a, J=7.5 Hz, 2H, 2-Ph-2H and -6H), 8.07 (m, 3H, 5-H and F-Ph-2H and -6-H).

¹³C-NMR (CDCl₃—CD₃OD): 23.56 (OCH₂CH₂), 25.81 (piper-3C and -5C), 40.10 (piper-4C), 51.72 (piper-2C and -6C), 54.39 (OCH₂CH₂CH₂), 65.22 (OCH₂), 100.90 (8-C), 106.18 (3-C), 114.62 (6-C), 115.60 (d, J=23 Hz, F-Ph-3C and -5C), 117.18 (4a-C), 125.84 (2-Ph-2C and -6C), 126.40 (5-C), 128.63 (2-Ph-3C and -5C), 130.81 (d, J=8 Hz, F-Ph-2C and -6C), 130.86 (2-Ph-1C), 131.42 (F-Ph-1C), 157.67 (8a-C), 162.80 (2-C), 163.71 (7-C), 165.65 (d, J=254 Hz, F-Ph-4C), 178.33 (4-C), 198.56 (Ph-C=O).

EXAMPLE 7

3-Chloro-7-[3-(4-p-fluorobenzoyl-1-piperidinyl)propoxy]-chromen-4-one hydrochloride The compound was obtained as a solid (yield=19%), melting point 240°–243° C.

Elemental analysis calculated for $C_{24}H_{23}ClFNO_4 \cdot HCl$: C 60.01; H 5.04; N 2.92; Cl 14.76. Found: C 59.85; H 5.02; N 2.70; Cl 14.60.

IR (KBr): 3200–3600, 2300–2600, 1680, 1640, 1625, 1597, 1443, 1230 cm⁻¹.

¹H-NMR (d₆-DMSO): 1.99 (m, 4H, piper-3H and -5H), 2.28 (m, 2H, OCH₂CH₂), 3.11 (m, 2H, piper-2H$_{ax}$ and -6H$_{ax}$), 3.24 (m, 2H, OCH₂CH₂CH₂), 3.61 (d a, J=11.7 Hz, 2H, piper-2H$_{eq}$ and -6H$_{eq}$), 3.68 (m, 1H, piper-4H), 4.26 (m, 2H, OCH₂), 7.15 (d, J=9.1 Hz, 1H, 6-H), 7.24 (s, 1H, 8-H), 7.40 (t, J=8 Hz, 2H, Ph-3H and -5H), 8.03 (d, J=9.1 Hz, 1H, 5-H), 8.11 (dd, J=8 and 5.7 Hz, 2H, Ph-2H and -6H)), 8.81 (s, 1H, 2H).

¹³C-NMR (d₆-DMSO): 23.60 (OCH₂CH₂), 26.16 (piper-3C and -5C), 40.40 (piper-4C), 51.60 (piper-2C and -6C), 53.81 ($OCH_2CH_2CH_2$), 66.58 ($OCH_2$), 101.83 (8-C), 116.14 (6-C), 116.32 (d, J=22 Hz, Ph-3C and -5C), 117.05 (3-C), 119.59 (4a-C), 131.71 (d, J=9 Hz, Ph-2C and -6C), 132.15 (d, J=2 Hz, Ph-1C), 153.99 (2-C), 157.71 (8a-C), 163.34 (7-C), 165.65 (d, J=250 Hz, Ph-4C), 170.79 (4-C), 199.71 (Ph-C=O).

EXAMPLE 8

7-[3-(4-p-fluorobenzoyl-1-piperidinyl)propoxy]-chromen-4-one hydrochloride

The compound was obtained as a solid (yield=26%), melting point 235°–238° C.

Elemental analysis calculated for $C_{25}H_{24}FNO_4 \cdot HCl$: C 64.64; H 5.65; N 3.14; Cl 7.95. Found:C 64.34; H 5.77; N 2.93; Cl 8.13.

IR (KBr): 3200–3600, 2300–2800, 1680, 1650, 1630, 1595, 1445, 1270, 1230 $cm^{-1}$.

$^1$H-NMR ($d_6$-DMSO): 2.01 (m, 4H, piper-3H and -5H), 2.30 (m, 2H, $OCH_2CH_2$), 3.13 (m, 2H, piper-$2H_{ax}$ and -$6H_{ax}$), 3.24 (t a, J=6Hz, 2H, $OCH_2CH_2CH_2$), 3.61 (d a, J =10.2 Hz, 2H, piper-$2H_{eq}$ and -$6H_{eq}$), 3.75 (m, 1H, 4-H), 4.25 (t a, J=6 Hz, 2H, $OCH_2$), 6.29 (d, J=6.3 Hz, 1H, 3-H), 7.08 (dd, J=9 and 2 Hz, 1H, 6-H), 7.16 (d, J=2 Hz, 1H, 8-H), 7.40 (t, J=9 Hz, 2H, Ph-3H and -5H), 7.96 (d, J=9 Hz, 1H, 5-H), 8.11 (dd, J=9 and 6 Hz, 2H, Ph-2H and -6H), 8.25 (d, J=6 Hz, 1H, 2-H).

$^{13}$C-NMR ($d_6$-DMSO): 22.93 ($OCH_2CH_2$), 25.46 (piper-3C and -5C), 40.03 (piper-4C), 50.85 (piper-2C and -6C), 53.18 ($OCH_2CH_2CH_2$), 65.77 ($OCH_2$), 101.77 (8-C), 111.91 (3-C), 114.62 (6-C), 115.65 (d, J=22 Hz, Ph-3C and -5C), 117.90 (4a-C), 26.13 (5-C), 131.04 (d, J=9 Hz, Ph-2C and -6C), 131.52 (d, J=3 Hz, Ph-1C), 156.16 (2-C), 157.34 (8a-C), 162.31 (7-C), 164.78 (d, J=250 Hz, Ph-4C), 175.25 (4-C), 199.09 (Ph-C=O).

EXAMPLE 9

7-(3-Chloropropoxy)-2-methylchromen-4-one 3.9 g (20 mmole) of 7-hydroxy-2-methylchromen-4-one, 4.4 ml (40 mmole) of 1-bromo-3-chloropropane and 6.1 g (40 mmole) of anhydrous potassium carbonate in 100 ml of acetone were mixed and refluxed under heating for 16 hours. The mixture was allowed to cool and the insoluble solid was separated by filtration. The filtrate was evaporated to dryness, and the residue obtained was suspended in ethyl ether, filtered, washed with ether and dried at vaccum to yield 4.76 g (85%) of the product, melting point 113°–115° C.

Elemental analysis calculated for $C_{13}H_{13}ClO_3$: C 61.79; H 5.19; Cl 14.03. Found: C 61.47; H 5.26; C 13.91.

IR (KBr): 3600–3200, 1640, 1600, 1240 $cm^{-1}$.

$^1$H-NMR ($CDCl_3$): 2.28 (quint., J=6 HZ, 2H, $OCH_2CH_2$), 2.35 (s, 3H, $CH_3$), 3.76 (t, J=6 Hz, 2H, $CH_2Cl$), 4.20 (t, J=6 Hz, 2H, $OCH_2$), 6.09 (s, 1H, 3-H), 6.82 (d, J=2.3 Hz, 1H, 8-H), 6.93 (dd, J=8.9 and 2.3 Hz, 1H, 6-H), 8.06 (d, J =8.9Hz, 1H, 5 -H).

$^{13}$C-NMR ($CDCl_3$): 20.36 (2-$CH_3$), 31.79 ($OCH_2CH_2$), 41.11 ($CH_2Cl$), 64.69 ($OCH_2$), 100.61 (8-C), 110.20 (3-C), 114.07 (6-C), 117.34 (4a-C), 126.79 (5-C), 157.89 (8a-C), 162.70 (7-C), 154.44 (2-C), 177.40 (4-C).

EXAMPLE 10

7-(3-Chloropropoxy)-3-methylchromen-4-one

Similarly, from 30 g (170 mmole) of 7-hydroxy-3-methyl-chromen-4-one and 25 ml (253 mmole) of 1-bromo-3-chloro-propane, 27 g (63%) of the product were obtained as a solid, melting point 83°–85° C.

Elemental analysis calculated for $C_{13}H_{13}ClO_3$: C 61.79; H 5.19; Cl 14.03. Found: C 61.58; H 5.22; C 13.83.

IR (KBr): 3600–3200, 1640, 1600, 1240 $cm^{-1}$.

$^1$H-NMR ($CDCl_3$): 2.00 (s, 3H, $CH_3$), 2.28 (quint., J=6 HZ, 2H, $OCH_2CH_2$), 3.76 (t, J=6 Hz, 2H, $CH_2Cl$), 4.19 (t, J=6 Hz, 2H, $OCH_2$), 6.80 (d, J=2.3 Hz, 1H, 8-H), 6.93 (dd, J=8.9 and 2.3 Hz, 1H, 6-H), 7.71 (d, J=0.9 Hz, 1H, 2-H), 8.12 (d, J=8.9 Hz, 1H, 5-H).

$^{13}$C-NMR ($CDCl_3$): 11.08 (3-$CH_3$), 31.81 ($OCH_2CH_2$), 41.12 ($CH_2Cl$), 64.69 ($OCH_2$), 100.48 (8-C), 114.32 (6-C), 117.55 (4a-C), 120.34 (3-C), 127.00 (5-C), 151.12 (2-C), 158.11 (8a-C), 162.58 (7-C), 177.42 (4-C).

EXAMPLE 11

7-(3-Chloropropoxy)-2-phenylchromen-4-one

Similarly, from 8.5 g (36 mmole) of 7-hydroxy-2-phenyl-chromen-4-one and 7 ml (71 mmole) of 1-bromo-3-chloro-propane, 10.7 g (96%) of the product were obtained as a solid, melting point 119°–121° C.

Elemental analysis calculated for $C_{18}H_{15}ClO_3$: C 68.68; H 4.80; Cl 11.30. Found: C 68.39; H 4.60; C 10.95.

IR (KBr): 1630, 1600, 1450, 1250, 1180 $cm^{-1}$.

$^1$H-NMR ($CDCl_3$): 2.29 (quint., J=6 HZ, 2H, $OCH_2CH_2$), 3.77 (t, J=6 Hz, 2H, $CH_2Cl$), 4.22 (t, J=6 Hz, 2H, $OCH_2$), 6.72 (s, H, 3-H), 6.94 (m, 2H, 6-H and 8-H), 7.49 (m, 3H, Ph-3H, -4H and -5H),7.86 (m, 2H, Ph-2H and -6H), 8.10 (d, J=9.6Hz, 1H, 5-H).

$^{13}$C-NMR ($CDCl_3$): 31.79 ($OCH_2CH_2$), 41.12 ($CH_2Cl$), 64.80 ($OCH_2$), 100.83 (8-C), 107.28 (3-C), 114.47 (6-C), 117.75 (4a-C), 125.91 (Ph-2C and -6C), 128.81 (Ph-3C) and -5H), 126.82 (5-C), 131.24 (Ph-4C), 131.54 (Ph-1C), 157.64 (8a-C), 162.71 (2-C), 162.99 (7-C), 177.48 (4-C).

EXAMPLE 12

7-(3-Chloropropoxy)-2-trifluoromethylchromen-4-one

Similarly, from 7-hydroxy-2-trifluoromethylchromen-4-one, the product was obtained as a solid (yield 69%), melting point 77°–79° C.

Elemental analysis calculated for $C_{13}H_{10}ClF_3O_3$: C 50.92; H 3.29; Cl 11.56. Found: C 50.63; H 3.04; C 11.30.

IR (KBr): 1670, 1610, 1430, 1200, 1130 $cm^{-1}$.

$^1$H-NMR ($CDCl_3$): 2.31 (t, J=6 HZ, 2H, $OCH_2CH_2$), 3.77 (quint, J=6 Hz, 2H, $CH_2Cl$), 4.26 (t, J=6 Hz, 2H, $OCH_2$), 6.67 (s, 1H, 3-H), 6.95 (d, J=1.9 Hz, 1H, 8-H), 7.03 (dd, J=9 and 1.9 Hz, 1H, 6-H), 8.10 (d, J=9 Hz, 1H, 5-H).

$^{13}$C-NMR ($CDCl_3$-$CD_3OD$): 31.82 ($OCH_2CH_2$), 41.06 ($CH_2Cl$), 65.16 ($OCH_2$), 101.01 (8-C), 110.63 (3-C), 115.86 (6-C), 117.87 (4a-C), 118.50 (q, J=272 Hz, $CF_3$), 127.26 (5-C), 151.80 (q, J=40 Hz, 2-C), 157.26 (8a-C), 163.90 (7-C), 175.82 (4-C).

EXAMPLE 13

4'-(3-Chloropropoxy)-2'-hydroxyacetophenone 10 g (66 mmole) of 2',4'-dihydroxyacetophenone, 10 ml (101 mmole) of 1-bromo-3-chloropropane and 22.7 g (164 mmole) of anhydrous potassium carbonate in 250 ml of acetone were mixed and refluxed under heating for 16 hours. The mixture was cooled to room temperature, the solid insoluble was separated by filtration, and the filtrate was evaporated to dryness. The residue was dispersed in ethyl ether, filtered and dried to give 13.1 g (87%) of the product, melting point 74° C.

IR (KBr): 3600–3200, 1650, 1590, 1285, 1160 cm$^{-1}$.

$^1$H-NMR (CDCl$_3$): 2.25 (quint, J=6 Hz, 2H, OCH$_2$CH$_2$), 2.56 (s, 3H, CH$_3$), 3.73 (t, J=6 Hz, 2H, CH$_2$Cl), 4.15 (t, J=6 Hz, 2H, OCH$_2$), 6.42 (m, 2H, 3-H and 5-H). 7.63 (d, J=8.1 Hz, 1H, 6-H), 12.73 (s, 1H,OH).

$^{13}$C-NMR (CDCl$_3$): 26.24 (CH$_3$), 31.90 (OCH$_2$CH$_2$), 41.20 (CH$_2$Cl), 64.53 (OCH$_2$), 101.34 (3-C), 107.56 (5-C), 113.89 (1-C), 132.20 (6-C), 164.90 (2-C and 4-C), 202.28 (C=O).

EXAMPLE 14

(E)-1-(4-(3 -Chloropropoxy)-2-hydroxyphenyl-3-dimethylamino-1-propenone 6 g (26 mmole) of the compound of Ex. 13 and 5.2 ml (39 mmole) of dimethylformamide-dimethylketal were mixed and refluxed under heating for 3.5 hours. The resultant solution was evaporated at vaccum, and the residue was suspended in 40 ml of ethyl ether. The solid obtained was filtered and dried at vaccum to give 5.6 g (75%) of the product as a solid, melting point 119°–121° C.

Elemental analysis calculated for C$_{14}$H$_{18}$ClNO$_3$: C 59.26; H 6.39; N 4.94; Cl 12.49. Found: C 58.89; H 6.33; N 4.91; Cl 12.20.

IR (KBr): 3600–3200, 1620, 1530, 1350, 1235, 1100 cm$^{-1}$.

$^1$H-NMR (CDCl$_3$): 2.24 (quint., J=6 HZ, 2H, OCH$_2$CH$_2$), 2.96 (s a, 3H, NCH$_3$), 3.18 (s a, 3H, NCH$_3$), 3.73 (t, J=6 Hz, 2H, CH$_2$Cl), 4.13 (t, J=6 Hz, 2H, OCH$_2$), 5.68 (d, J=12 Hz, 1H, =CH—N), 6.38 (d, J=8.6 Hz, 1H, Ph-5H), 6.41 (s, 1H, Ph-3H), 7.61 (d, J=8.6 Hz, 1H, Ph-6H), 7.84 (d, J=12 Hz, 1H, CO—CH=).

$^{13}$C-NMR (CDCl$_3$): 31.96 (OCH$_2$CH$_2$), 37.28 (NCH$_3$), 41.25 (CH$_2$Cl), 45.20 (NCH$_3$), 64.15 (OCH$_2$), 89.59 (=CH—N), 101.48 (Ph-3C), 106.31 (Ph-5C), 113.81 (Ph-1C), 129.45 (Ph-6C), 153.73 (CO—CH=), 163.04 (Ph-2C), 16s.13 (Ph-4C), 190.17 (C=O).

EXAMPLE 15

7-(3-Chloropropoxy)chromen-4-one

To a solution of 3 g (11 mmole) of the compound of Ex. 14 in 60 ml of chloroform, 2 ml of hydrochloric acid 5.6M solution in ethanol were added. The mixture was stirred at room temperature for 15 min. The chloroform solution was washed with water and sodium bicarbonate aqueous solution, and evaporated to dryness. The residue was dispersed in ethyl ether, filtered and dried to give 2 g (70%) of the product as a white solid, melting point 76°–78° C.

Elemental analysis calculated for C$_{12}$H$_{11}$ClO$_3$: C 60.39; H 4.65; Cl 14.85. Found: C 60.22; H 4.71; Cl 14.78.

IR (KBr): 1650, 1625, 1605, 1260, 1230 cm$^{-1}$.

$^1$H-NMR (CDCl$_3$): 2.30 (quint., J=6 HZ, 2H, OCH$_2$CH$_2$), 3.77 (t, J=6 Hz, 2H, CH$_2$Cl), 4.22 (t, J=6 Hz, 2H, OCH$_2$), 6.28 (d, J=6 Hz, 1H, 3-H), 6.86 (d, J=2.3 Hz, 1H, 8-H), 6.97 (dd, J=8.8 and 2.3 Hz, 1H, 6-H), 7.78 (d, J=6 Hz, 1H, 2-H), 8.12 (d, J=8.8 Hz, 1H, 5-H).

$^{13}$C-NMR (CDCl$_3$): 31.76 (OCH$_2$CH$_2$), 41.09 (CH$_2$Cl), 64.74 (OCH$_2$), 100.78 (8-C), 112.66 (3-C), 114-47 (6-C), 118.61 (4a-C), 126.90 (5 -C), 154.62 (2 -C), 157.83 (8a-C), 162.79 (7-C), 176.57 (4-C).

EXAMPLE 16

3-Chloro-7-(3-chloropropoxy)chromen-4-one

To a solution of 4.5 g (16 mmole) of 1-(4-(3-chloropropoxy)-2-hydroxyphenyl)-3-dimethylamino-1-propenone in 60 ml of chloroform was added a solution of 1.9 g (16 mmole) of tert-butyl hypochlorite in 40 ml of chloroform at a temperature between 0° C. and 5° C. The mixture was allowed to stir for 4 hours at room temperature and evaporated to dryness. The residue was washed with diisopropyl ether to give 2.9 g (67%) of the product as a solid, melting point 101°–103° C.

Elemental analysis calculated for C$_{12}$H$_{10}$Cl$_2$O$_3$: C 52.77; H 3.69; Cl 25.96. Found: C 52.61; H 3.75; Cl 26.21.

IR (KBr): 1635, 1610, 1255, 1220 cm$^{-1}$.

$^1$H-NMR (CDCl$_3$): 2.30 (quint., J=6 HZ, 2H, OCH$_2$CH$_2$), 3.77 (t, J=6 Hz, 2H, CH$_2$Cl), 4.23 (t, J=6 Hz, 2H, OCH$_2$), 6.87 (d, J=2.4 Hz, 1H, 8-H), 7.02 (dd, J=9 and 2.4 Hz, 1H, 6-H), 8.10 (s, 1H, 2-H), 8.16 (d, J=9Hz, 1H, 5-H).

$^{13}$C-NMR (CDCl$_3$): 31.81 (OCH$_2$CH$_2$), 41.08 (CH$_2$Cl), 65.00 (OCH$_2$), 100.72 (8-C), 115.38 (6-C), 117.20 (4a-C), 120.61 (3-C), 127.50 (5-C), 151.53 (2-C), 157.58 (8a-C), 163.25 (7-C), 171.51 (4-C).

EXAMPLE 17

7-(3-Chloropropoxy)-3-formyl-chromen-4-one

A solution of 20 g (87 mmole) of 4'-(3-chloropropoxy)-2'-hydroxy-acetophenone in 80 ml de N,N-dimethylformamide was cooled on an ice bath, and 30 ml (214 mmole) of phosphoryl chloride were dropwise added. The mixture was stirred for 30 min at 0° C., and allowed to stand at room temperature for an additional 16 hours. The reaction crude was poured onto ice and removed with chloroform. The chloroform extracts were washed 4 times with water, dried over anhydrous sodium sulfate and evaporated in vacuo. The oil obtained was purified by column chromatography (silica gel-chloroform) to give 12 g (51%) of the product.

Elemental analysis. Calculated for C$_{13}$H$_{11}$ClO$_4$: C, 58.55; H, 4.16; Cl, 13.29. Found: C, 58.20; H, 4.25; Cl, 12.97.

IR (KBr): 1695, 1650, 1620 cm$^{-1}$.

$^1$H-RMN (CDCl$_3$): 2.31 (quint., J=6Hz, 2H, O—CH$_2$—CH$_2$), 3.78 (t, J=6Hz, 2H, CH$_2$-Cl), 4.25 (t, J=6Hz, 2H, O—CH$_2$), 6.94 (d, J=2Hz, 1H, 8-H), 7.04 (dd, J=9 and 2Hz, 1H, 6-H), 8.18 (d, J=9Hz, 1H, 5-H), 8.47 (s, 1H, 2-H), 10.35 (s, 1H, CHO).

$^{13}$C-NMR (CDCl$_3$): 31.73 (O—CH$_2$—CH$_2$), 41.02 (CH$_2$Cl), 65.07 (OCH$_2$), 101.55 (8-C), 115.53 (6-C), 118.72 (4a-C), 120.01 (3-C), 127.31 (5-C), 157.58 (8a-C), 160.01 (2-C), 163.64 (7-C), 174.88 (4-C), 188.45 (CHO).

EXAMPLE 18

7-(3-Chloropropoxy)-3-(hydroxymethyl)chromen-4-one

To a solution of 2.5 g (9.4 mole) of the aforesaid product in 15 ml of chloroform, 15 ml of absolute ethanol were added and cooled to a temperature of −10° C. 0.2 g (5.3 mole) of sodium borohydride in several portions were added and then stirred for 15 min at −10° C. and for an additional 1 hour at 0° C. The reaction mixture was poured onto water, neutralized by addition of hydrochloric acid, and removed with chloroform. The extracts were dried over anhydrous sodium sulfate and evaporated to give an oil, which was purified by column chromatography (chloroform-methanol, 98:2 as eluant). 1 g (40%) of the product was obtained.

Elemental analysis. Calculated for C$_{13}$H$_{13}$ClO$_4$: C, 58.11; H, 4.88; Cl, 13.19. Found: C, 58.03; H, 4.97; Cl, 12.90.

$^1$H-NMR (CDCl$_3$): 2.21 (m, 2H, —O—CH$_2$—CH$_2$), 3.68 (t, J=6Hz, 2H, CH$_2$—Cl), 4.12 (t, J=6Hz, 2H, O—CH$_2$—CH$_2$), 4.47 (s, 2H, CH$_2$—OH), 6.76 (d, J=2Hz, 1H, 8-H), 6.88 (dd, J=9 and 2Hz, 1H, 6-H), 7.81 (s, 1H, 2-H), 8.00 (d, J=9Hz, 1H, 5-H).

EXAMPLE 19

Injection formulation
Composition for 1 ampoule:
7-[3-(4-p-Fluorobenzoyl-1-piperidinyl)propoxy] chromen-4-one hydrochloride 5.0 mg
Methyl p-hydroxybenzoate 1.0 mg
Propyl p-hydroxybenzoate 0.1 mg
Bidistilled water to volume 2.0 ml

EXAMPLE 20

0.1% oral solution formulation
7-[3-(4-p-Fluorobenzoyl-1-piperidinyl)propoxy] chromen-4-one hydrochloride 1000 mg
Methyl p-hydroxybenzoate 135 mg
Propyl p-hydroxybenzoate 15 mg
70% 20 g
Sodium saccharin 50 mg
Orange scent 0.25 ml
Distilled water to volume 100 ml

EXAMPLE 21

Tablet formulation
Composition for 10 mg tablet:
7-[3-(4-p-Fluorobenzoyl-1-piperidinyl)propoxy] chromen-4-one hydrochloride 10.0 mg
Corn starch 43.2 mg
Talc 6.0 mg
Hydrogenated castor oil 2.0 mg
Lactose to volume 200.0 mg

EXAMPLE 22

Tablet formulation
Composition for 50 mg tablet:
7-[3-(4-p-Fluorobenzoyl-1-piperidinyl)propoxy] chromen-4-one hydrochloride 50.0 mg
Corn starch 86.4 mg
Talc 12.0 mg
Hydrogenated castor oil 4.0 mg
Lactose to volume 400.0 mg

We claim:

1. A chromene compound having the formula (I):

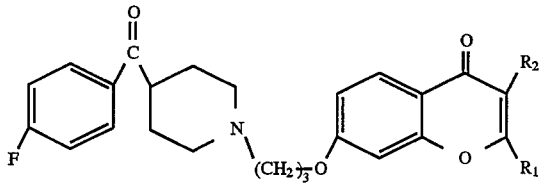

(I)

wherein $R_1$ and $R_2$ are hydrogen, alkyl having from 1 to 4 carbon atoms, halogen, trifluoromethyl, optionally substituted phenyl or hydroxymethyl, or a pharmaceutically acceptable addition salt thereof.

2. A compound selected from the group consisting of 7-[3-(4-p-fluorobenzoyl-1-piperidinyl)propoxy]-chromen-4-one; 7-[3-(4-p-fluorobenzoyl-1-piperidinyl)propoxy]-3-methyl-chromen-4-one; and 3-Hydroxymethyl-7-[3-(4-p-fluorobenzoyl-1-piperidinyl)propoxy]chromen-4-one; or a pharmaceutically acceptable addition salt thereof.

3. A pharmaceutical composition comprising an effective amount of at least one compound of claim 1, optionally in combination with pharmaceutically acceptable carriers and/or adjuvants.

4. A pharmaceutical composition comprising an effective amount of at least one compound of claim 2, optionally in combination with pharmaceutically acceptable carriers and/or adjuvants.

5. A method of treatment of psychosis and schizophrenia which comprises administering to a mammal in need thereof an effective amount of at least one compound according to claim 1.

6. A method of treatment of psychosis and schizophrenia which comprises administering to a mammal in need thereof an effective amount of at least one compound according to claim 2.

7. A process for preparing the chromene compounds of claim 1 or 2 which comprises alkylating 4-(p-fluorobenzoyl) piperidine of formula II

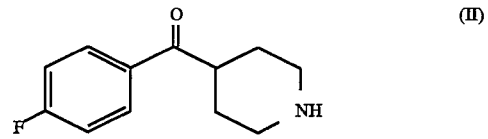

(II)

with a 7-(3-halopropoxy)chromen-4-one of formula III

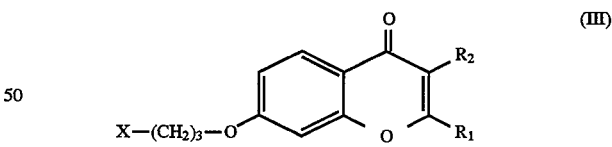

(III)

wherein X is chlorine, bromine or iodine and $R_1$ and $R_2$ are as defined in claim 1, and if desired, converting a compound of formula I in free base form into an acid addition salt thereof.

* * * * *